US00PP09250P

United States Patent [19]

Egger

[11] Patent Number: Plant 9,250

[45] Date of Patent: Aug. 15, 1995

[54] LONGIFLORUM×ASIATIC HYBRID LILY PLANT NAMED 'CEB MAGIC'

[75] Inventor: Donald L. Egger, Aurora, Oreg.

[73] Assignee: Cebeco Lilies, Inc., Aurora, Oreg.

[21] Appl. No.: 333,502

[22] Filed: Nov. 2, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

*Attorney, Agent, or Firm*—Klarquist Sparkman Campbell Leigh & Whinston

[57] ABSTRACT

A new and distinct lily hybrid named 'Ceb Magic' characterized by upright, very large vibrant orange colored flowers on tall, strong stems excellent for cut flower production.

1 Drawing Sheet

BACKGROUND OF THE INVENTION

The present invention comprises a new and distinct cultivar of lily hybrid, referred to commercially as a *Longiflorum-Asiatic* Lily Hybrid, referred to by the cultivar name 'Ceb Magic'.

This invention is the product of a controlled breeding program in Aurora, Oreg. The seed parent was a proprietary non-released unnamed (ACE×Chiefwood) seedling. The pollen parent was PAM #2, another proprietray non-released plant.

The *Longiflorum-Asiatic* cross is relatively new to the trade. This type of cross was originally made to create colored *Lilium longiflorum* hybrids. Instead, due to the difficulty in crossing back to *L. longiflorum,* the plants that were developed had to be crossed with Asiatic lilies. As such, the results look more like Asiatic lilies. The resulting hybrids often have several advantages, not necessarily in combination, over an Asiatic lily: (1) often larger flowers; (2) often larger, waxier leaves; (3 ) hybrid vigor; (4) lower susceptibility to scorch; (5) excellent flower texture and substance; (6) more virus resistance; (7) new and clearer colors; and (8) stronger, sturdier stems.

This invention has not been observed under all possible environmental conditions. The phenotype may vary significantly with variations in environment such as temperature, light intensity, and day length, without, however, any variation in genotype. The following traits have been repeatedly observed in asexually propagated progeny and are determined to be the basic characteristics of this invention which in combination distinguish this lily as a new and distinct cultivar: (1) very large, upright flowers of a vibrant orange with some spots around the nectary; (2) good bud color; (3) tall, vigorous, uniform strong stems; (4) excellent vase life; (5) early bloom time; (6) good fragrance; and (7) a nonfading flower. Bulbs of this plant may be precooled and forced out of season for very uniform cut flower production.

To the inventor's knowledge, there are no other *Longiflorum-Asiatic* lily hybrids with this color flower suitable for cut flower forcing on the market.

Asexual reproduction of this new variety has been initially and subsequently accomplished at Cebeco Lilies, Inc. in Aurora, Oreg., by scaling and tissue culture. The resulting plants have shown that the above-mentioned unique features are stable and reproduce true to type in each successive propagation.

Figure 2:
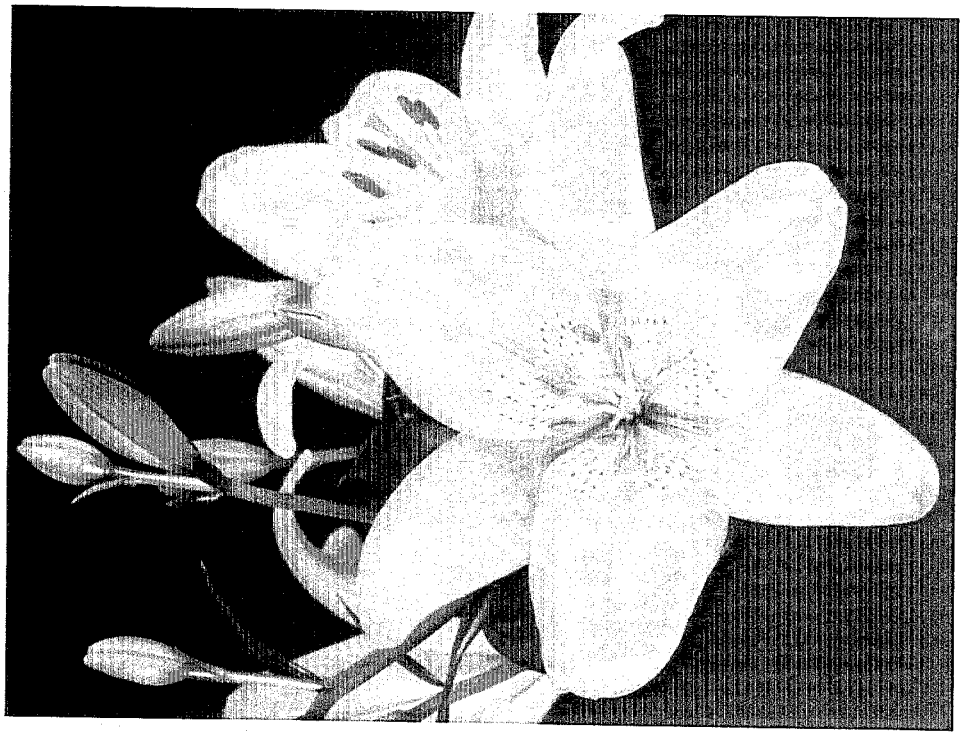
FIG. 2 is a close-up photograph which illustrates in greater detail a single flower of the new plant.
Figure 1:
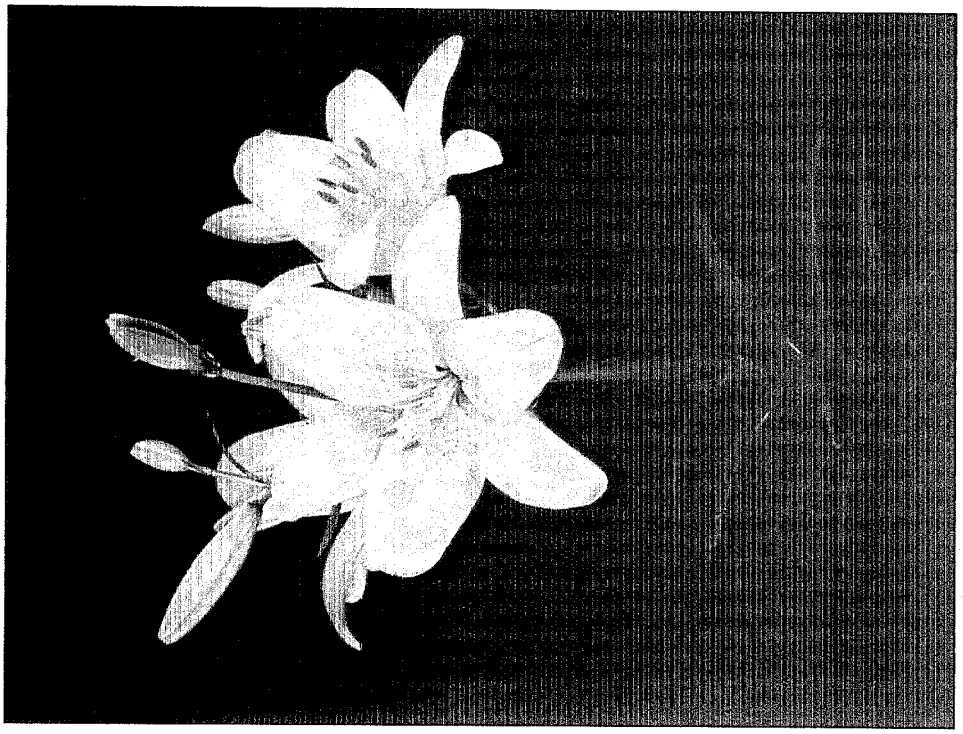
FIG. 1 is a photograph shhowing the 'Ceb Magic' lily.

The photographs of the drawing were taken in August 1993 in a studio and illustrate the typical flower and foliage form, with color being as true as is reasonably possible in this type of color photograph.

DETAILED DESCRIPTION

The following is a detailed description of the invention based on plants produced under commercial practices in the Cebeco Lilies, Inc. greenhouses in Aurora, Oreg. in July 1993. Color references are made to The Royal Horticultural Society Colour Chart (RHS), except where the context indicates a term having its ordinary dictionary meaning.

THE PLANT

Origin: Seedling.

Parentage:

*Seed parent.*—Unnamed (Ace×Chiefwood).

*Pollen parent.*—PAM #2.

Commercial classification: Upright *Longiflorum-Asiatic* hybrid, cut flower type.

Classification: Division VIII, according to the Horticultural Classification of Lilies by The Royal Horticultural Society of London.

Form: Single erect stem bearing terminal cluster of flowers.

Height: About 74–97 cm. from the top of the soil to the top of the flowers from bulds of 12 cm. on circumference.

Growth habit: Vigorous, upright and rigid.

Foliage:

*Arrangement.*—Spiral.

*Quantity.*—Average.

*Leaf size.*—Variable from about 11–16 cm. long and 18–35 mm. wide.

*Leaf shape.*—Lanceolate with entire margins.

*Texture.*—Leathery.

*Aspect.*—Glossy.

*Color.*—Medium green on both sides, closest to 147A.

Bulbs:

*Size.*—Variable, ranging to about 12–14 cm. in circumference as used commercially.

*Color.*—White.

THE BUD

Size: Very large, to about 10.3 cm. long and 3.3 cm. wide just prior to opening.

Shape: Ovoid with an obtuse tip.

Rate of opening: The mature bud opens slowly in response to light.

Color: Orange with yellow green at tips. Orange Group 28C to 25C. Tepal edges are Orange Group 28B.

THE FLOWER

Blooming habit: Annually, once and early season.

Days to bloom: Flowers approximately 78 days after spring greenhouse planting under typical commercial flower forcing conditions of 15° Celsius night time temperatures.

Inflorescence size: About 23 cm. high and 31 cm. wide when there are five flowers present.

Flower size: Very large.

*Diameter.*—About 20 cm.

*Depth.*—About 10 cm.

Borne: In an umbel or modified raceme of typically about 5 flowers from bulbs, 12–14 cm. in circumference.

Shape: When the flower first opens it is V-shaped. Later, the shape flattens out and the tepals reflex slightly at the tips.

Tepalage:

*Number.*—Six.

*Arrangement.*—Imbricated.

*Shape.*—Ovate.

*Texture.*—Leathery, thick.

*Aspect.*—Satiny.

*Size.*—Length: About 12 cm. Width: Inner tepals — about 60 mm. Outer tepals — about 42 mm. Depth of imbrication: About 17 mm.

*Nectary.*—About 3.5 cm. long; orange; pubescent; with the channels close together.

*Projections.*—There are raised lines like the nectary channels to sides of nectary with short hairs. A few of the spots are raised and pubescent.

*Spots.*—Oval on the bottom ⅓ of the tepal. Grayed-Purple 187B.

*Blush.*—None.

*Color.*—Topside: Vibrant Orange. Orange Group 28B-25A. Lightens to 25B with age. Bottomside: Orange Group 28A on edges to 24C in middle.

*Discoloration.*—Base of tepals lighten with age giving the flower a "white eye" look.

*Fragrance.*—Moderate.

*Lasting quality.*—Excellent.

Pedicel:

*Length.*—Variable. From 2–13 cm.

*Color.*—Yellow-green.

*Orientation.*—Ascending upwardly from about 45° from the horizontal.

THE REPRODUCTIVE ORGANS

Stamens:

*Number.*—Six, typical of the genus Lilium.

*Anthers before dehiscence.*—Size: About 2 cm. Color: Grayed-Orange Group 166D.

*Filaments.*—Length: About 7.6 cm. Color: Orange. Orange Group 24D.

*Pollen.*—Color: Orange, Grayed-Orange Group 169C.

Pistil:

*Number.*—One.

*Style.*—Length: About 6.8 cm. Color: Orange Group 29A near stigma to Orange Group 28C in the middle to Orange Group 20C at base.

*Stigma.*—Color: Orange, Orange Group 29A.

THE FRUIT

Fertility: The fruit is infertile.

Shape: Ovoid.

Color at maturity: Soft brown.

I claim:

1. A new and distinct cultivar of *Longiflorum-Asiatic* hybrid lily plant substantially as herein shown and described.

* * * * *